United States Patent
Andersson et al.

(10) Patent No.: US 9,812,306 B2
(45) Date of Patent: Nov. 7, 2017

(54) SHIFT CORRECTION FOR SPECTRAL ANALYSIS

(75) Inventors: Greger Andersson, Oxford, CT (US); Kevin Judge, Danbury, CT (US)

(73) Assignee: SMITHS DETECTION INC., Edgewood, MD (US)

( * ) Notice: Subject to any disclaimer, the term of this patent is extended or adjusted under 35 U.S.C. 154(b) by 814 days.

(21) Appl. No.: 14/239,209

(22) PCT Filed: Aug. 17, 2012

(86) PCT No.: PCT/US2012/051440
§ 371 (c)(1),
(2), (4) Date: May 20, 2014

(87) PCT Pub. No.: WO2013/026026
PCT Pub. Date: Feb. 21, 2013

(65) Prior Publication Data
US 2014/0324362 A1   Oct. 30, 2014

Related U.S. Application Data

(60) Provisional application No. 61/524,689, filed on Aug. 17, 2011.

(51) Int. Cl.
*H01J 49/00* (2006.01)
*G06F 19/00* (2011.01)

(52) U.S. Cl.
CPC ........ *H01J 49/0036* (2013.01); *G06F 19/703* (2013.01)

(58) Field of Classification Search
CPC ... G06F 19/703; H01J 49/0036; H01J 49/009; H01J 49/0027

USPC ........... 702/19, 28, 66, 76, 77, 85; 250/282, 250/288; 700/30
See application file for complete search history.

(56) References Cited

U.S. PATENT DOCUMENTS

| | | | |
|---|---|---|---|
| 6,906,320 B2 | 6/2005 | Sachs et al. | |
| 6,983,213 B2 | 1/2006 | Wang | |
| 7,279,679 B2 | 10/2007 | Old et al. | |
| 7,493,225 B2 * | 2/2009 | Wang ................. | G06K 9/00496 250/282 |

(Continued)

FOREIGN PATENT DOCUMENTS

| | | |
|---|---|---|
| GB | 2422009 A | 7/2006 |
| JP | 2004506216 A | 2/2004 |

(Continued)

OTHER PUBLICATIONS

Carson P. K. et al: "Exponentially Weighted Moving Average (EWMA) Control Charts for Monitoring an Analytical Process", Industrial & Engineering Chemistry Research, vol. 47, No. 2, Dec. 12, 2007, pp. 405-411.

(Continued)

*Primary Examiner* — John H Le
(74) *Attorney, Agent, or Firm* — Casimir Jones SC

(57) ABSTRACT

Techniques are described for resolving and identifying peaks of signal intensity in mass chromatograms so that the peaks may be associated with components (e.g., chemical and/or ionic species) representative of an analysis sample to identify the components. The techniques facilitate correction of shift errors in the peaks of signal intensity of the mass chromatograms.

20 Claims, 6 Drawing Sheets

(56) References Cited

U.S. PATENT DOCUMENTS

| | | |
|---|---|---|
| 7,809,450 B2 | 10/2010 | Lev-Ami et al. |
| 7,987,060 B2 | 7/2011 | Lange et al. |
| 2004/0181351 A1 | 9/2004 | Thompson et al. |
| 2004/0195500 A1 | 10/2004 | Sachs et al. |
| 2005/0061968 A1 | 3/2005 | Green |
| 2006/0255258 A1 | 11/2006 | Wang et al. |
| 2007/0221835 A1 | 9/2007 | Raftery et al. |
| 2008/0015785 A1 | 1/2008 | Mujezinovic et al. |
| 2008/0243407 A1 | 10/2008 | Cetto |
| 2009/0001261 A1 | 1/2009 | Yamaguchi et al. |
| 2009/0294645 A1 | 12/2009 | Gorenstein et al. |

FOREIGN PATENT DOCUMENTS

| | | |
|---|---|---|
| JP | 2006184275 A | 7/2006 |
| JP | 2009156722 A | 7/2009 |
| WO | 200213228 A2 | 2/2002 |
| WO | 2004038602 A1 | 5/2004 |

OTHER PUBLICATIONS

He et al., "Comparison of a new spectrum alignment algorithm with other methods" 2010 American Control Conference Marriott Waterfront, Baltimore, MD, USA, Jun. 30-Jul. 2, 2010. p. 1260-1265.

Gorban et al. (eds.), "Principal Manifolds for Data Visualization and Dimension Reduction," LNCSE 58 (Springer, New York (2007)).

Jolliffe, "Principal Component Analysis" in the Springer Series in Statistics, 2nd ed. (Springer, NewYork (2002)).

Kay, Fundamentals of Statistical Signal Processing. (Upper Saddle River, New Jersey: Prentice Hall (1993)).

Scharf, Statistical Signal Processing: Detection, Estimation, and Time Series Analysis. (Boston: Addison-Wesley (1991)).

International Search Report and Written Opinion for PCT/US2012/051440 dated Nov. 2, 2012, 13 pages.

\* cited by examiner

SHIFT CORRECTION FOR SPECTRAL ANALYSIS

CROSS-REFERENCE TO RELATED APPLICATIONS

The present application claims the benefit of 35 U.S.C. §119(e) of U.S. Provisional Application Ser. No. 61/524,689, filed Aug. 17, 2012, and titled "SHIFT CORRECTION FOR SPECTRAL ANALYSIS," which is herein incorporated by reference in its entirety.

BACKGROUND

A mass chromatogram is a representation of mass spectrometry data as a chromatogram, where the x-axis represents mass-to-charge and the y-axis represents signal intensity. Mass chromatograms are often employed in instances where mass spectrometry is used in conjunction with some form of chromatography, such as in or gas chromatography-mass spectrometry (GC-MS) or liquid chromatography-mass spectrometry (LC-MS). In such instances, the x-axis of the mass chromatogram represents retention time, while the y-axis represents signal intensity or relative signal intensity. There are many different types of metrics that the intensity may represent, depending on the information that is extracted from each mass spectrum. For example, a total ion current (TIC) chromatogram represents the summed intensity across the entire range of masses being detected at all points in the analysis. The range of masses in a TIC is typically several hundred mass-to-charge units or more.

SUMMARY

Techniques are described for resolving and identifying peaks of signal intensity in a variety of analytical techniques including ion mobility spectroscopy (e.g., mass chromatogram correction), mass spectroscopy, infrared spectroscopy. The techniques facilitate correction of shift errors in the peaks of signal intensity of the mass chromatograms.

The techniques may be implemented as a method comprising accessing mass spectrometry data stored in a tangible memory, wherein the mass spectrometry data describes signal intensity and ionization time for a sample analyzed by a mass spectrometer, and wherein the mass spectrometry data is configured to facilitate the representation of signal intensity versus mass-to-charge for the sample in at least two mass chromatograms; processing the mass spectrometry data to identify significant regions for analysis the mass chromatograms; identifying peaks in signal intensity within the identified significant regions of each of the mass chromatograms; correcting the peaks in signal intensity with respect to the mass-to-charge in the mass chromatograms; aligning consecutive ones of the at least two mass chromatograms to identify at least one aligned peak in signal intensity; and identifying one or more components of the sample from the at least one aligned peak in signal intensity.

The techniques may also be implemented in a data processing apparatus. The data processing apparatus includes a tangible memory operable to store mass spectrometry data describing signal intensity and ionization time for a sample analyzed by a mass spectrometer. The mass spectrometry data is configured to facilitate the representation of signal intensity versus mass-to-charge for the sample in at least two mass chromatograms. The tangible memory may further be operable to store a module configured to facilitate analysis of the at least two mass chromatograms. The data processing apparatus further includes a processing system operable to execute the module to: process the mass spectrometry data to identify significant regions for analysis of each of the mass chromatograms; identify peaks in signal intensity within the identified significant regions of each of the mass chromatograms; correct the peaks in signal intensity with respect to the mass-to-charge in each of the mass chromatograms; align consecutively ones of the at least two mass chromatograms to identify at least one aligned peak in signal intensity; and identify one or more components of the sample from the at least one aligned peak in signal intensity.

The techniques may further be implemented in a mass spectrometry system. The mass spectrometry system includes a mass spectrometer and a data processing apparatus. The mass spectrometer is configured to ionize a sample to generate charged molecules, fragments, etc., and to measure the mass-to-charge ratio of the charged molecules and generate mass spectrometry data in response thereto, wherein the mass spectrometry data describes signal intensity and ionization time for the sample. The data processing apparatus is configured to receive the mass spectrometry data from the mass spectrometer, the mass spectrometry data configured to facilitate the representation of signal intensity versus mass-to-charge for the sample in at least two mass chromatograms; process the mass spectrometry data to identify significant regions for analysis of each of the mass chromatograms; identify peaks in signal intensity within the identified significant regions of each of the mass chromatograms; correct the peaks in signal intensity with respect to the mass-to-charge in each of the mass chromatograms; align consecutively one of the at least two mass chromatograms to identify at least one aligned peak in signal intensity; and identify one or more components of the sample from the at least one aligned peak in signal intensity.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

DETAILED DESCRIPTION

Figure 1:
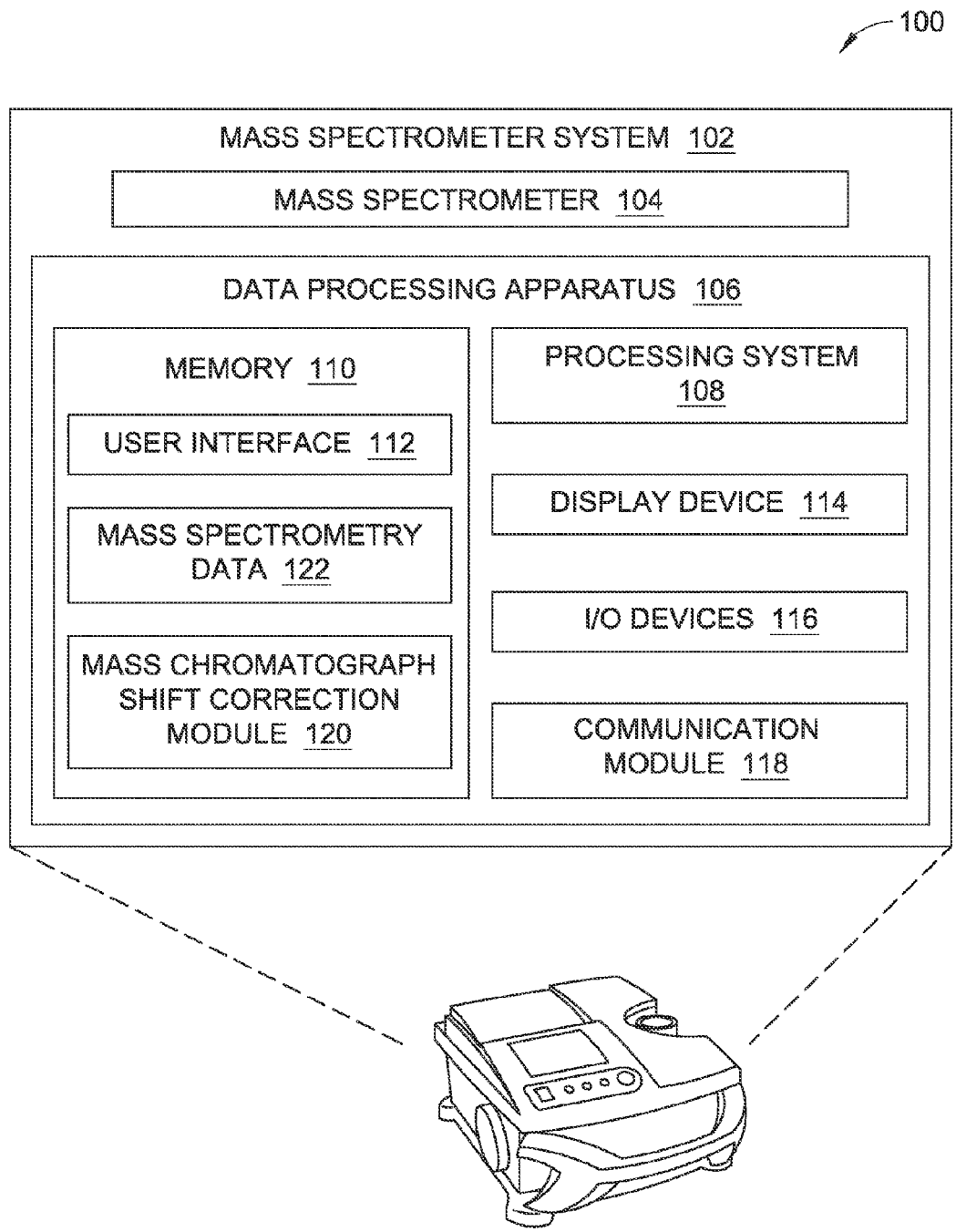
FIG. 1 is a block diagram in an example implementation, in which a mass spectrometer system is configured with a data processing apparatus operable to resolve and identify peaks of signal intensity in mass chromatograms so that the peaks may be associated with components (e.g., chemical and/or ionic species) representative of an analysis sample to identify the components.

Mass chromatograms are subject to various types of errors that can complicate or prevent the determination of peaks and the subsequent assignment of peaks to chemical entities. For example, high concentrations of components in a sample, non-ideal interactions among small and large ions, and electronic drift in the mass spectrometer cause shifts in mass spectral peaks that belie their association with the chemical species and/or ions from which they originated. Such variability can complicate the determination of the chemical species present within a sample. For example, uncorrected peaks arising in different locations in two analyses of the same sample may have originated from a sample comprising two component chemicals or from a sample comprising one component chemical whose peaks were shifted in one analysis but not the other.

Techniques are described for resolving and identifying peaks of signal intensity in mass chromatograms so that the peaks may be associated with components (e.g., chemical and/or ionic species) representative of an analysis sample to identify the components. The techniques facilitate correction of shift errors (e.g., x axis shifting) in the peaks of signal intensity of the mass chromatograms. In accordance with an example implementation of the techniques, mass spectrometry data stored in a tangible memory is accessed. The mass spectrometry data describes signal intensity and ionization time for a sample analyzed by a mass spectrometer, and may be configured to facilitate the representation of signal intensity versus mass-to-charge for the sample in at least two mass chromatograms. The mass spectrometry data is processed to identify significant regions for analysis of each of the mass chromatograms. Peaks in signal intensity within the identified significant regions of each of the mass chromatograms are then identified. The peaks in signal intensity are then corrected with respect to the mass-to-charge in each of the mass chromatograms. Consecutive mass chromatograms are aligned to identify at least one aligned peak in signal intensity. One or more components (e.g., chemical and/or ionic species) of the sample may then be identified from the at least one aligned peak in signal intensity.

The techniques may be implemented as a program of instruction stored in memory and executed by the processing system of a data processing apparatus. In implementations, the data processing apparatus may be associated with (e.g., may be a component part of, may receive data from) a mass spectrometer of a mass spectrometry system such as a liquid chromatography-mass spectrometry (LC-MS) system, a gas chromatography-mass spectrometry (GC-MS) system, an ion mobility spectrometer (IMS) system, and so forth. However, in other implementations, the data processing apparatus may be a stand-alone data processing device such as a computer, personal computer, laptop computer, tablet, and so forth.

"mass chromatogram" can refer to a graphical representation of mass spectrometry data as a chromatogram, where the x-axis represents time, mass-to-charge, etc. and the y-axis represents signal intensity. A common use of this data representation is when mass spectrometry is used in conjunction with some form of chromatography, e.g., liquid chromatography-mass spectrometry (LC-MS), gas chromatography-mass spectrometry (GC-MS), and so forth. In such instances, the x-axis of the mass chromatogram represents time, analogous to any other chromatograms, e.g., an IMS plasmagram, an infrared spectra, and so forth while the y-axis represents signal intensity or relative signal intensity.

FIG. 1 illustrates an environment 100, in an example implementation, that includes a mass spectrometer system 102 in accordance with the present disclosure. As shown, the mass spectrometer system 102 includes a mass spectrometer 104 and a data processing apparatus 106 that is operable to resolve and identify peaks of signal intensity in mass chromatograms so that the peaks may be associated with components (e.g., chemical and/or ionic species) representative of a sample analyzed by the mass spectrometer 104 to identify the components.

The mass spectrometer 104 is configured to receive one or more samples to be analyzed. The mass spectrometer 104 measures the mass-to-charge ratio of charged particles for determining the masses of the particles to identify the elemental composition of a sample being analyzed. Generally, the mass spectrometer 104 includes an ion source that converts gas phase sample molecules into ions. A mass analyzer sorts the ions by their masses by applying electromagnetic fields to the ion stream. A detector may then measure the value of an indicator quantity such as signal intensity and provides data (e.g., signal intensity and ionization time) suitable for calculating the abundances of each component that is present in the sample. The mass spectrometry data may be configured to facilitate representation of signal intensity versus time, mass-to-charge, and so forth, for the sample in mass chromatograms in accordance with the present disclosure.

It is contemplated that the mass spectrometer 104 may employ a variety of mass spectrometry techniques. Thus, the mass spectrometer 104 may be configured in a variety of ways. For example, the mass spectrometer 104 may be used in conjunction with some form of chromatography, e.g., liquid chromatography-mass spectrometry (LC-MS), gas chromatography-mass spectrometry (GC-MS), and so forth. Thus, in implementations, the mass spectrometer 104 may comprise a liquid chromatography-mass spectrometer (LC-MS), gas chromatography-mass spectrometer (GC-MS), and so forth. Other examples include, but are not limited to, an ion mobility spectrometer (IMS), an infrared spectrometer, e.g., a FTIR.

In implementations, the mass spectrometer 104, including some or all of its components, can operate under computer control. For example, a controller can be included with or in mass spectrometer 104 to control the components and functions of mass spectrometer described herein using software, firmware, hardware (e.g., fixed logic circuitry), manual processing, or a combination thereof. In implementations, controller functionality may be furnished to the mass spectrometer 104 by the data processing apparatus 106. However, it is contemplated that the mass spectrometer 104 may include a separate controller. The terms "controller" "functionality," "service," and "logic" as used herein generally represent software, firmware, hardware, or a combination of software, firmware, or hardware in conjunction with controlling the mass spectrometer 104. In the case of a software implementation, the module, functionality, or logic represents program code that performs specified tasks when executed on a processor (e.g., CPU or CPUs). The program code may be stored in one or more computer-readable memory devices (e.g., internal memory and/or one or more tangible media), and so on. The structures, functions, approaches, and techniques described herein can be implemented on a variety of commercial computing platforms having a variety of processors.

The data processing apparatus 106 may include a processing system 108 and a memory 110. The processing system 108 provides processing functionality for the data processing apparatus 106 and may include any number of processors, micro-controllers, or other processing systems, and resident or external memory for storing data and other information accessed or generated by the data processing apparatus 106. The processing system 108 may execute one or more software programs which implement techniques described herein. The processing system 108 is not limited by the materials from which it is formed or the processing mechanisms employed therein, and as such, may be implemented via semiconductor(s) and/or transistors (e.g., using electronic integrated circuit (IC) components), and so forth.

The memory 110 is an example of tangible computer-readable media that provides storage functionality to store various data associated with operation of the data processing apparatus 106, such as software programs and/or code segments, or other data to instruct the processing system 108 and possibly other components of the data processing apparatus 106 to perform the steps described herein. Thus, the memory can store data, such as a program of instructions for operating the mass spectrometer 104 (including its components), spectral data, and so on. Although a single memory 110 is shown, a wide variety of types and combinations of memory (e.g., tangible memory, non-transitory) may be employed. The memory 110 may be integral with the processing system 108, may comprise stand-alone memory, or may be a combination of both.

The memory 110 may include, but is not necessarily limited to: removable and non-removable memory components, such as Random Access Memory (RAM), Read-Only Memory (ROM), Flash memory (e.g., a Secure Digital (SD) memory card, a mini-SD memory card, and/or a micro-SD memory card), magnetic memory, optical memory, Universal Serial Bus (USB) memory devices, hard disk memory, external memory, and other types of computer-readable storage media. In implementations, the memory 110 may include removable Integrated Circuit Card (ICC) memory, such as memory provided by a Subscriber Identity Module (SIM) card, a Universal Subscriber Identity Module (USIM) card, a Universal Integrated Circuit Card (UICC), and so on.

The data processing apparatus 106 is illustrated as including a user interface 112, which is storable in memory 110 and executable by the processor 108. The user interface 150 is representative of functionality to control the display of information and data to the user of the data processing apparatus 106 and/or mass spectrometry system 102 via a display device 114.

The display device 114 is configured to display information to a user of the data processing apparatus 106 and/or the mass spectrometry system 102. In embodiments, the display device 114 may comprise an LCD (Liquid Crystal Diode) display, a TFT (Thin Film Transistor) LCD display, an LEP (Light Emitting Polymer) or PLED (Polymer Light Emitting Diode) display, and so forth, configured to display text and/or graphical information such as a graphical user interface. The display device 114 may be backlit via a backlight such that it may be viewed in the dark or other low-light environments. In some implementations, the display device 114 may not be integrated into the mobile electronic device and may instead be connected externally using universal serial bus (USB), Ethernet, serial connections, and so forth.

The display device 114 may be provided with a touch screen for entry of data and commands. For example, a user may operate the data processing apparatus 106 by touching the touch screen and/or by performing gestures on the screen. In some embodiments, the touch screen may be a capacitive touch screen, a resistive touch screen, an infrared touch screen, combinations thereof, and so forth. The user interface 112 may provide functionality to allow the user to interact with one or more applications (e.g., software programs) stored in memory 110 and executed by the processing system 108 of the data processing apparatus 106 by providing inputs via the touch screen of the display device 114 and/or one or more input/output (I/O) devices 116 (e.g., a keypad, buttons, a wireless input device, a thumbwheel input device, a track stick input device, a touchpad input device, a microphone, speakers, and so on). For example, the user interface 112 may cause an application programming interface (API) to be generated to expose functionality to an application to configure the application for display by the display device 114 or in combination with another display. In embodiments, the API may further expose functionality to configure the application to allow the user to interact with an application by providing inputs via the touch screen and/or the I/O devices 116.

The data processing apparatus 106 may further include a communication module 118. The communication module 118 is representative of communication functionality to permit the data processing apparatus and/or the mass spectrometer system 102 to send/receive data between different devices (e.g., components/peripherals) and/or over a network. The communication module 118 may be representative of a variety of communication components and functionality including, but not limited to: one or more antennas; a browser; a transmitter and/or receiver; a wireless radio; data ports; software interfaces and drivers; networking interfaces; data processing components; and so forth.

The communication module 118 may be operatively configured to provide communication between the data processing apparatus and the mass spectrometer 104. The communication module 118 is also communicatively coupled with the processing system 108 (e.g., for communicating inputs from the mass spectrometer 104 to the processing system 108). The communication module 118 and/or the processing system 108 can also be configured to communicate with a variety of different networks, including, but not necessarily limited to: the Internet, a cellular telephone network, a local area network (LAN), a wide area network (WAN), a wireless network, a public telephone network, an intranet, and so on.

In FIG. 1, the data processing apparatus is illustrated as including a mass chromatograph shift correction module 120, which may be implemented as a software application stored in memory 110 and executed by the processing system 108 of the data processing apparatus 106. The mass chromatograph shift correction module 120 is representative of mass chromatograph processing functionality that is provided by the data processing apparatus 106. The mass chromatograph processing functionality allows the data processing apparatus 106 to resolve and identify peaks of signal intensity in mass chromatograms so that the peaks may be associated with components (e.g., chemical and/or ionic species) representative of an analysis sample to identify the components. The mass chromatograph processing functionality further facilitates correction of shift errors in the peaks of signal intensity of the mass chromatograms. For example, in implementations, the mass chromatograph processing module 120 causes the data processing apparatus 106 to implement the techniques and processes described herein below in the discussion of FIGS. 2 through 7 to resolve and identify peaks of signal intensity in the mass chromatograms so that the peaks may be associated with components (e.g., chemical and/or ionic species) representative of an analysis sample to identify the components.

As shown in FIG. 1, mass spectrometry data 122 furnished by the mass spectrometer 104 may be stored in memory 110. The mass spectrometry data 122 may describe signal intensity and time for a sample analyzed by the mass spectrometer 104. The mass spectrometry data 122 may be configured to facilitate the representation of signal intensity versus ionization time for the sample in at least two mass chromatograms. For example, the mass spectrometer 104 may be configured to furnish mass spectrometry data 122 to the data processing apparatus 106. The mass chromatograph shift correction module 120, when executed by the processing system 108, may cause the mass spectrometry data 122 to be stored in memory 110, either permanently, or temporarily pending processing as discussed below. In implementations, the mass spectrometry data 122 may be formatted by the mass spectrometer 104 (e.g., by the controller of the mass spectrometer 104) to facilitate creation of mass chromatograms by the mass chromatograph shift correction module 120. However, in other implementations, the mass spectrometry data 122 may be unformatted (or incorrectly formatted). In such instances, the mass chromatograph shift correction module 120 may include functionality to format the mass spectrometry data to facilitate the creation of mass chromatograms either before storage in memory 110 or during processing of the data 122. When executed by the processing system 108, the mass chromatograph shift correction module 120 causes the mass spectrometry data 122 stored in memory 110 to be accessed by the processing system 108 (e.g., retrieved from memory 110 for processing).

Generally, any of the functions described herein can be implemented using software, firmware, hardware (e.g., fixed logic circuitry), manual processing, or a combination of these implementations. The terms "module" and "functionality" as used herein generally represent software, firmware, hardware, or a combination thereof. In the case of a software implementation, for instance, the term module represents executable instructions (e.g., program code) that perform specified tasks when executed on a processor, such as one or more processors in the processing system 108 of the data processing apparatus of FIG. 1. The executable instructions can be stored in one or more computer readable media, an example of which is the memory 110 of the data processing apparatus 106 of FIG. 1. However, the features of the techniques described below may be platform-independent, meaning that, in implementations, the techniques may be implemented on a variety of commercial computing platforms having a variety of processors.

The following discussion describes techniques to resolve and identify peaks of signal intensity in mass chromatograms so that the peaks may be associated with components (e.g., chemical and/or ionic species) representative of an analysis sample to identify the components. Aspects of the procedures described may be implemented in hardware, firmware, or software, or a combination thereof. The procedures are shown as a set of blocks that specify operations performed by one or more devices and are not necessarily limited to the orders shown for performing the operations by the respective blocks. In portions of the following discussion, reference will be made to the environment 100 of FIG. 1 and/or the mass chromatograms and matrices illustrated in FIGS. 3 through 7.

Figure 2A:
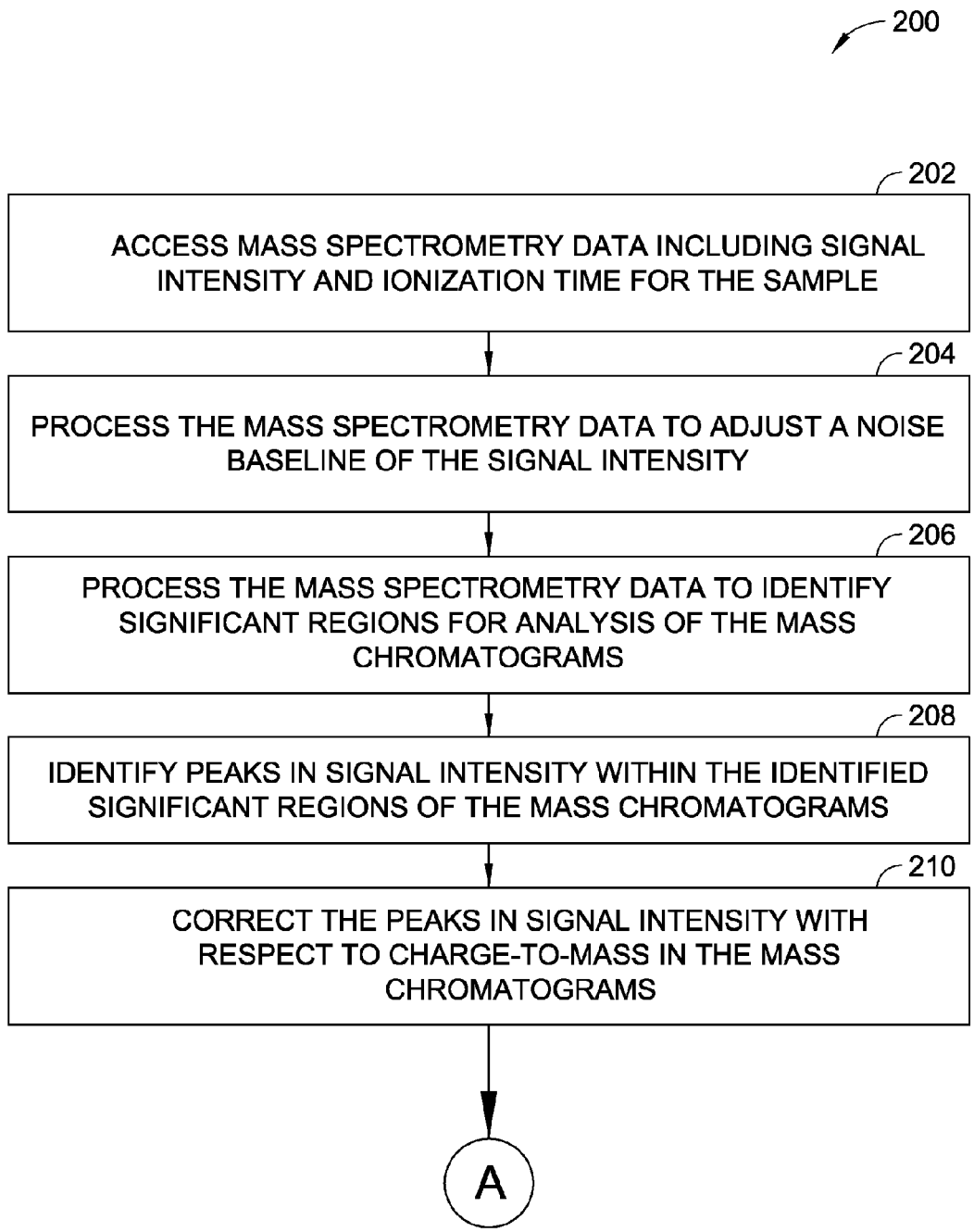
FIGS. 2A and 2B are flow diagrams illustrating a method in an example implementation to resolve and identify peaks of signal intensity in mass chromatograms so that the peaks may be associated with components (e.g., chemical and/or ionic species) representative of an analysis sample to identify the components.
Figure 2B:
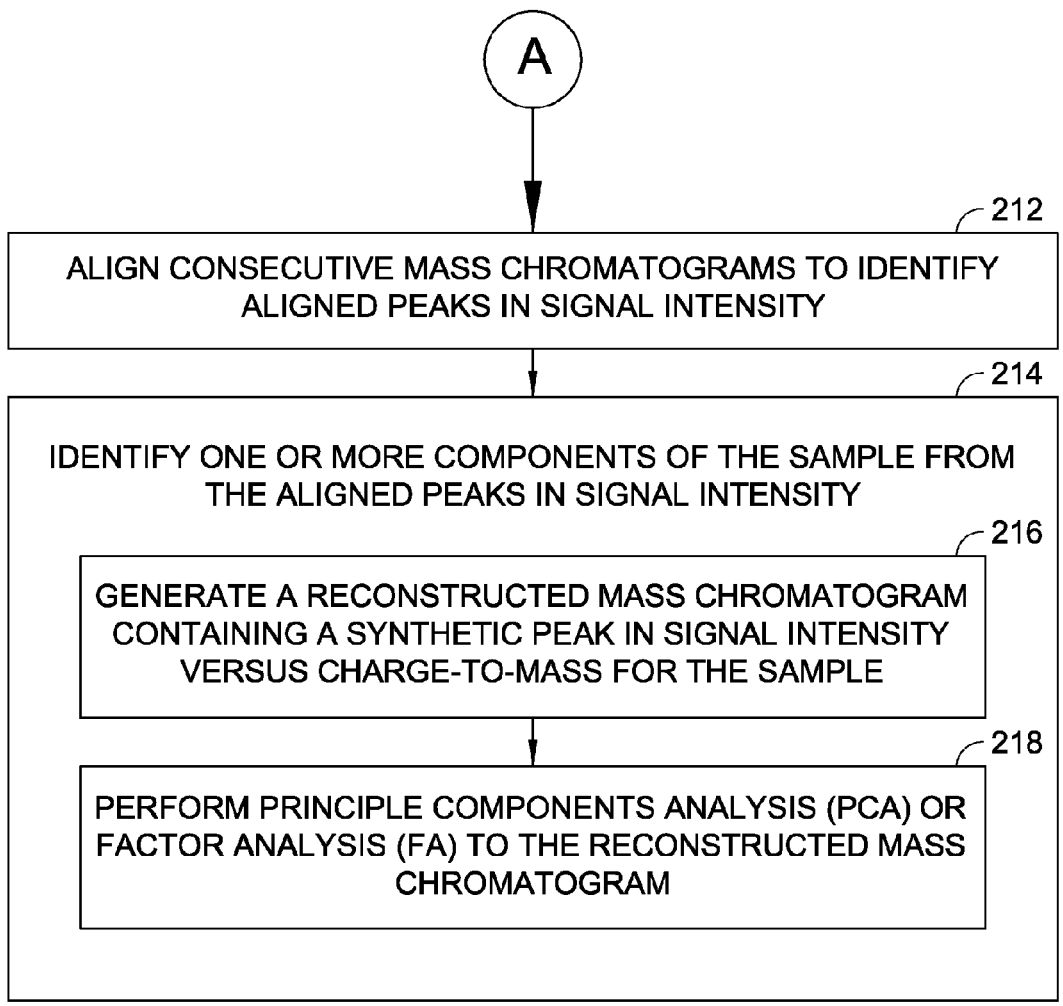

FIGS. 2A and 2B depict a procedure (method or process) 200, in an example implementation, to resolve and identify peaks of signal intensity in mass chromatograms so that the peaks may be associated with components (e.g., chemical and/or ionic species) representative of an analysis sample to identify the components. As illustrated, mass spectrometry data configured to facilitate the representation of signal intensity versus mass-to-charge for the sample in at least two mass chromatograms is accessed (Block 202). For example, as described in the discussion of FIG. 1, mass spectrometry data 122 stored in memory 110 may be accessed by the processing system 108 (e.g., retrieved from memory 110 for processing).

Figure 3:
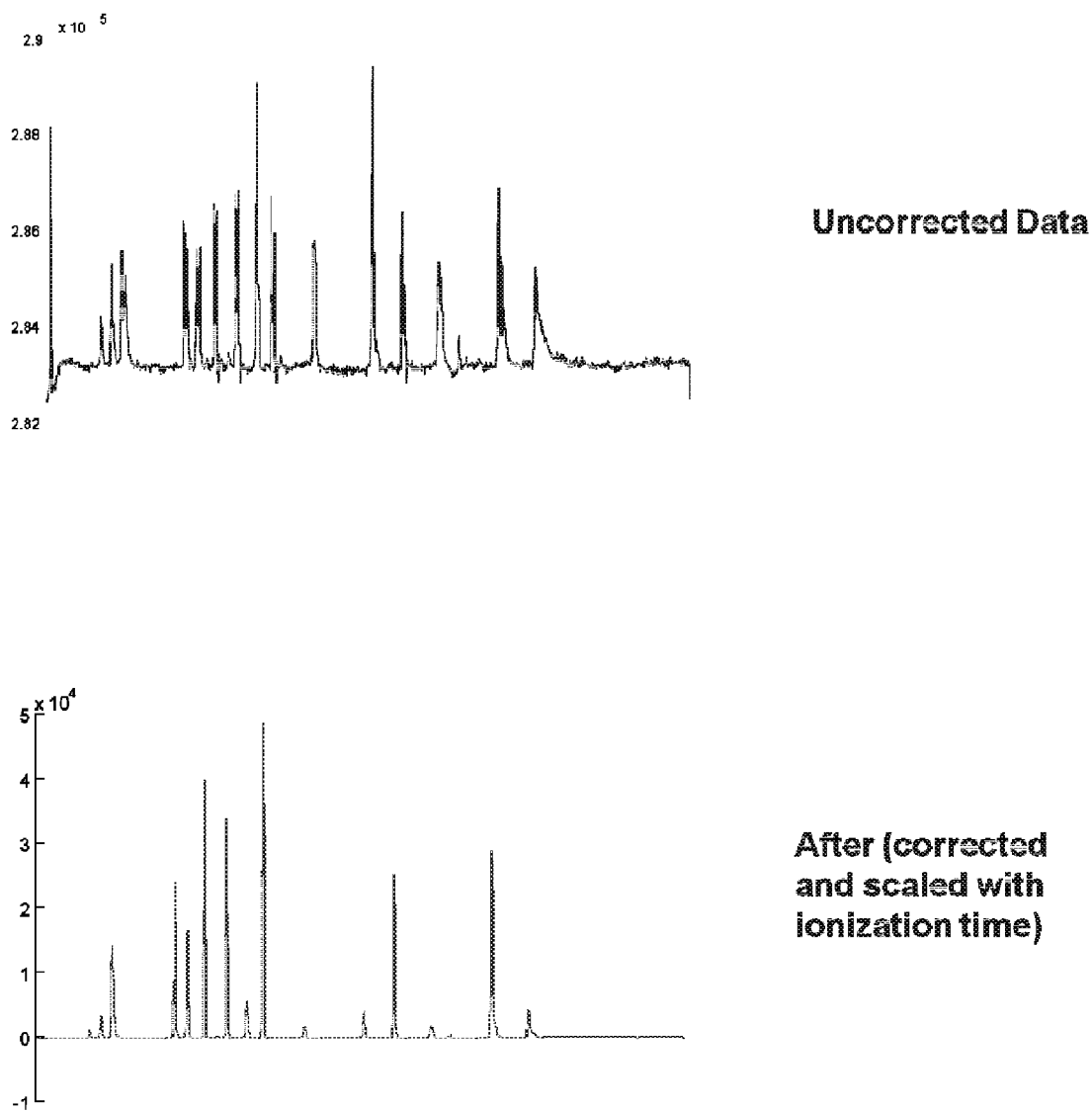
FIG. 3 is a graph illustrating mass spectrometry data is processed to adjust a noise baseline of and scale the signal intensity with respect to ionization time.

The mass spectrometry data is processed to adjust a noise baseline of the signal intensity for a plot of signal intensity versus time (Block 204). For example, as shown in FIG. 3, the mass spectrometry data used to create the illustrated mass chromatogram is corrected so that the noise baseline of the mass chromatogram is adjusted (moved) to zero (0). The mass spectrometry data is further scaled with respect to ionization time. In this manner, noise in the signal intensity is reduced and/or removed from the mass chromatogram.

Figure 4:
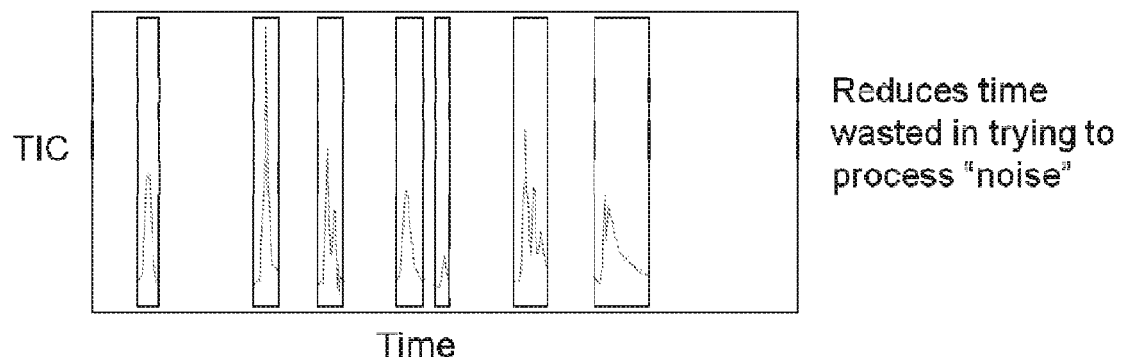
FIG. 4 is a graph further illustrating the mass chromatogram of FIG. 3, wherein the mass spectrometry data has been processed to identify significant regions for analysis of the mass chromatogram by applying an exponentially weighted moving average (EWMA) to the mass spectrometry data.
Figure 5:
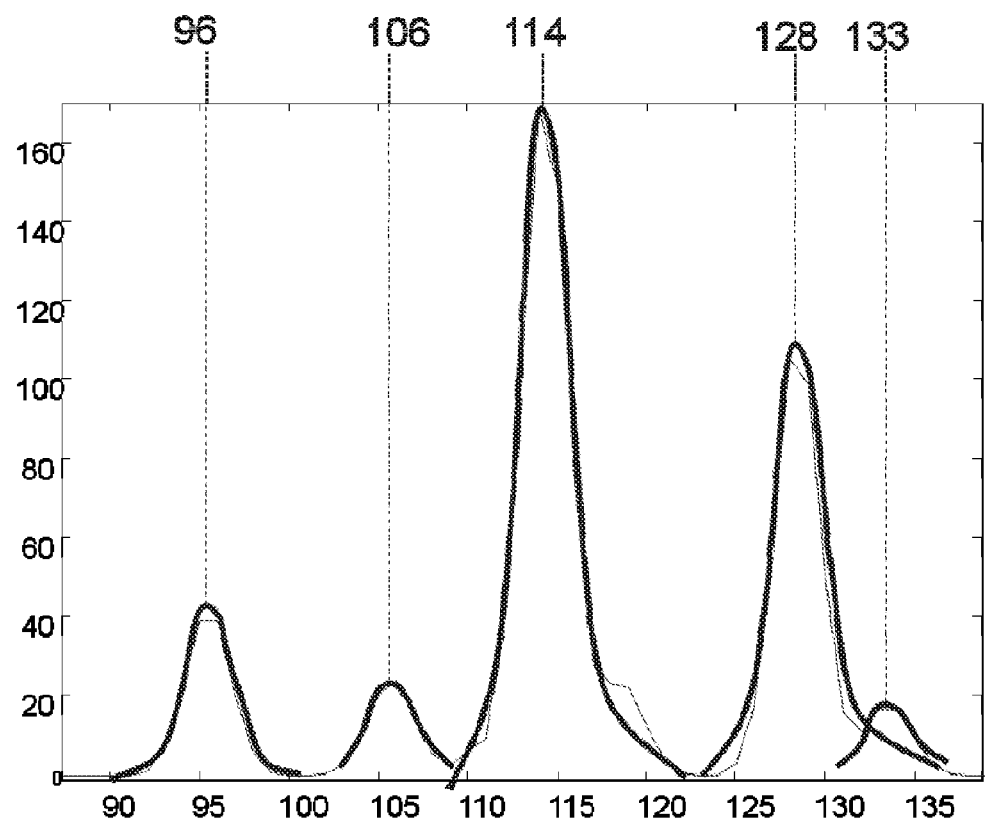
FIG. 5 is a graph further illustrating the mass chromatogram of FIGS. 3 and 4, wherein peaks in signal intensity within the identified significant regions the mass chromatogram are identified by approximating the peaks using a Gaussian approximation and assigning the peaks to bins.
Figure 6:
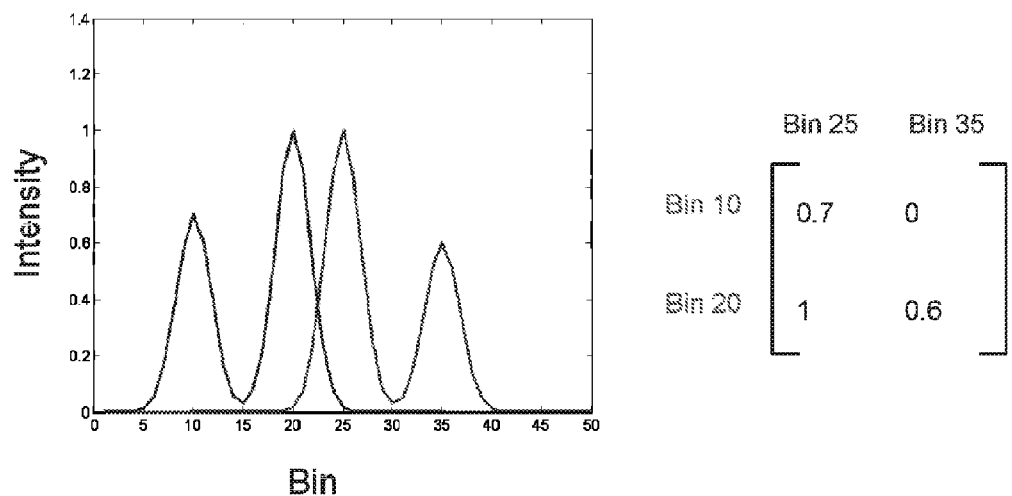
FIG. 6 is a graph further illustrating alignment of the mass chromatogram of FIGS. 3, 4, and 5 with a consecutive mass chromatogram using a peak alignment matrix to identify aligned peaks in signal intensity.

The mass spectrometry data is further processed to identify significant regions for analysis of each of the mass chromatograms (Block 206). Thus, the present techniques provide for reducing the complexity of analysis (and thus reducing processing time) by identifying the potentially significant regions (e.g., regions may be associated with charged fragments, the charged molecule (M+ peak), and so forth, in the chromatogram and limiting the subsequent analysis to those regions. The significant regions are those regions of the mass chromatogram that are deemed to contain information by a metric for discerning signal from noise. For example, as shown in FIG. 4, the signal may be differentiated from noise, and thus the significant regions may be identified, by applying an exponentially weighted moving average (EWMA) technique to the chromatogram (e.g., to the mass spectrometry data) and identifying data points that are at least a predetermined number of standard deviations from the mean sample intensity. Portions of the chromatogram that are defined by this data are defined to be the significant regions. In FIG. 4, data points that are at least three (3) standard deviations from the mean sample intensity of the chromatogram are identified. However, other criteria and metrics can be used to distinguish signal from noise. For example, EWMA techniques can be used with a different requirement for selecting data points (e.g., 1, 1.5, 2, 2.5, 4, or some other whole or fractional number of standard deviations from the mean sample intensity). Discrimination of signal from noise can embody a number of techniques. Suitable example techniques are discussed in Scharf, Louis L., *Statistical Signal Processing: Detection, Estimation, and Time Series Analysis*. Boston: Addison-Wesley (1991) and Kay, Steven M., *Fundamentals of Statistical Signal Processing*. Upper Saddle River, N.J.: Prentice Hall (1993), which are herein incorporated by reference in their entireties.

Peaks of signal intensity within the significant regions may then be analyzed. For instance, as shown in FIG. 2A, peaks in signal intensity within the identified significant regions of each of the mass chromatograms may be identified (Block 208).

In implementations, the location and area of peaks in signal intensity within the significant regions are identified by approximating the peaks with a Gaussian approximation. However, other peak characteristics may are determined. For example, in embodiments, the peak height and the full-width at half maximum of peaks within the identified significant regions may be identified. Moreover, it is contemplated that mathematical approximations other than Gaussian approximations may be employed. Example mathematical approximations suitable for use with the present disclosure may include, but are not necessarily limited to: Lorentzian approximation, Voigt approximations (e.g., a convolution of a Gaussian approximation and a Lorentzian approximation), exponentially modified Gaussian approximation (e.g., a convolution between a Gaussian approximation and an exponential decay approximation), a convolution between two exponential decay approximations, and log-normal approximations.

In embodiments, the point of maximum intensity within a significant region is identified and a Gaussian (or other approximation) is calculated around that point. If the Gaussian explains a large enough fraction of the putative peak, the peak location and area are added to a peak table. The Gaussian is subtracted from the chromatogram and the process continues (the procedure step of Block 208 is repeated) with the new point of maximum intensity that is above the noise threshold. The process continues (the procedure step of Block 208 is repeated) until no more data points remain that are above the noise threshold.

The peaks in signal intensity may be corrected with respect to mass-to-charge in the mass chromatograms (Block 210). In embodiments, the peaks may be corrected with respect to the x-axis (e.g., time) using bin-shifting techniques. Using bin shifting, the x-axis is divided into an arbitrary number of discrete bins. For example, example mass chromatograms may be divided into four thousand (4000) time-ordered bins. Peaks are then assigned to the bin into which the peak maximum falls. The number of the bin into which the peak maximum falls is used to identify that peak, and is recorded in a peak table associated with the chromatogram. For example, as shown in FIG. 3, a mass chromatogram with Gaussian-fit peak maxima falling in bins 96, 106, 114, 128, and 133 results in the values 96, 106, 114, 128, and 133 (with the values in the bins being associated with mass-to-charge of the fragment, molecule, so forth) being recorded in the peak table associated with the chromatogram. As shown, the first peak will have the lowest bin number and the last peak will have the highest bin number.

Correction of peaks (e.g., values in the peak table) is aided by comparing multiple chromatograms acquired from the same sample and/or multiple peak tables constructed from the same sample. For example, in implementations, multiple (e.g., 2, 3, 4, 5, 6, 7, 8, 9, 10, 20, 50, or more) chromatograms are acquired, and/or multiple (e.g., 2, 3, 4, 5, 6, 7, 8, 9, 10, 20, 50, or more), which may be a corresponding number of, peak tables are constructed for the same sample.

In some embodiments, the peaks in a series of chromatograms acquired from the same sample may be aligned. The alignment associates the peaks in two or more chromatograms that resulted from the same chemical species and/or ion in the analyzed sample that produced the two or more chromatograms. For example, as shown in FIG. 2B, two consecutive chromatograms are aligned to identify aligned peaks in signal intensity (Block 212). In embodiments, consecutively acquired chromatograms (e.g., the first and the second chromatograms, the second and the third chromatograms, the third and the fourth chromatograms, and so forth) may be aligned through the construction of a peak alignment matrix, as shown in FIG. 4. In such embodiments, the aligned peaks may be associated with each other through the use of a linked list. Each entry in the peak alignment matrix is the product of a first peak area from a first chromatogram and a second peak area from the next chromatogram for that sample. Thus, for a first chromatogram C including peaks $\{p_i \ldots p_n\}$ and having peak areas $\{a_i \ldots a_n\}$, and the next consecutively acquired chromatogram D from the same sample including peaks $\{q_j \ldots q_m\}$ and having peak areas $\{b_j \ldots b_m\}$ the matrix is constructed by finding all entries $x_{ij}=a_i*b_j$ by iterating i over 1 through n and j over 1 through m. In some embodiments, when the difference in bin number for two peaks is greater than a defined threshold (e.g., a difference of 5 or more, 10 or more, 15 or more, 20 or more, 25 or more, and so forth), a zero (0) is entered into the matrix for that peak pair.

Analysis of matrix entries provides a metric for assessing the appropriateness of an alignment. For instance, in one or more embodiments, summing entries along a matrix diagonal indicates how one chromatogram may be shifted with respect to the other chromatogram. For example, for two chromatograms, each including four peaks and thus producing a 4×4 square matrix, comparing the sum $(x_{11}+x_{22}+x_{33}+x_{44})$ with the sum $(x_{12}+x_{23}+x_{34})$ provides a metric to determine the better of the two following peak alignments:
1) peak 1 in chromatogram 1 aligned with peak 1 in chromatogram 2
   peak 2 in chromatogram 1 aligned with peak 2 in chromatogram 2
   peak 3 in chromatogram 1 aligned with peak 3 in chromatogram 2
   peak 4 in chromatogram 1 aligned with peak 4 in chromatogram 2
   or,
2) peak 1 in chromatogram 1 aligned with peak 2 in chromatogram 2
   peak 2 in chromatogram 1 aligned with peak 3 in chromatogram 2
   peak 3 in chromatogram 1 aligned with peak 4 in chromatogram 2

In the second peak alignment, each chromatogram has an extra peak without a match in the other chromatogram. Moreover, in implementations, other metrics and matrix transformations may be used to provide a metric for chromatogram alignment. For example, comparison of chromatograms need not be limited to comparison of pairs of consecutive chromatograms. In one or more embodiments, all pair-wise combinations of chromatograms may be analyzed to determine peak associations among sets of chromatograms for the same sample. Such analysis may be used, for example, to resolve small peaks that are close together in the chromatogram, and that may be significant in some chromatograms of the set, but not in others.

In implementations, empirical data may be used to correct peak locations. For example, a constraint in some implementations is that errors in peak location only result in peak shifts to higher bins. Thus, in such implementations, correcting of peaks may be performed by only shifting peaks to lower bins. In addition, the peak shifts need not necessarily be the same for all peaks in sample intensity in a chromatogram. Thus, peaks may be corrected by different amounts. Moreover, peaks are not reordered when aligned. Thus, in such implementations, all nth peaks in a chromatogram may be aligned with the (n+k)th peak in the next chromatogram, where k is an integer (e.g., k is selected from the set { . . . , −5, −4, −3, −2, −1, 0, 1, 2, 3, 4, 5, . . . }).

Figure 7:
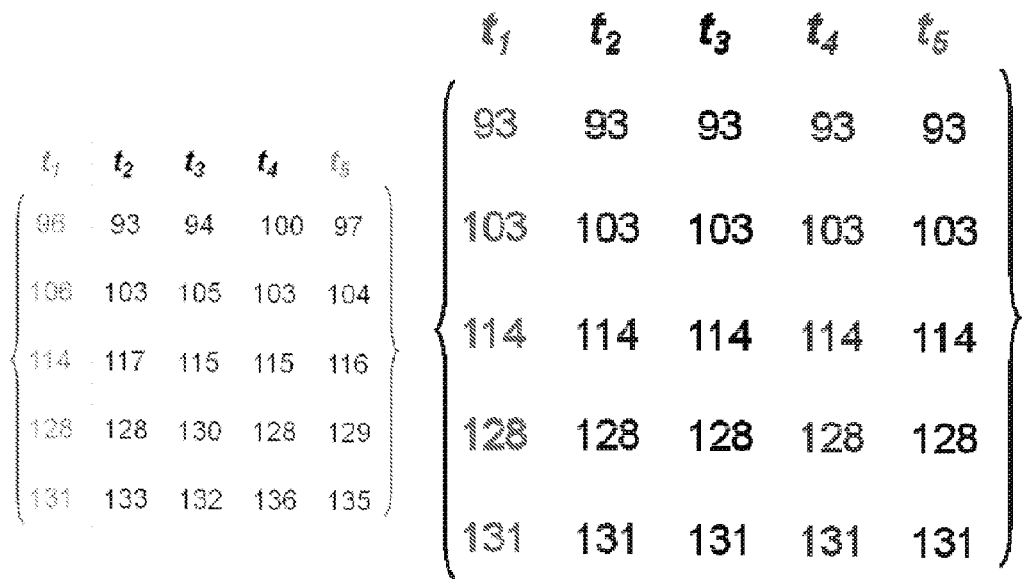
FIG. 7 is a depiction of a matrix generated from the peak alignment matrix of each mass chromatogram so that the aligned peaks are in rows and the peaks of each chromatogram are in columns, wherein bin numbers are assigned to the peaks in the peak tables by determining the minimum bin value in each row (e.g., the lowest bin value for each set of matched peaks) and assigning that value to all peaks in the row.

After peak associations are determined for pairs of consecutive chromatograms, the chromatograms and/or peak tables are corrected for bin shift by determining the optimal peak alignment and the peak tables are aligned accordingly. As shown in FIG. 7, a matrix may be generated from the peak tables such that the aligned peaks are in rows and the peaks of each chromatogram are in a column. Bin numbers may be assigned to the peaks in the peak tables by determining the minimum bin value in each row (e.g., the lowest bin value for each set of matched peaks) and assigning that value to all peaks in the row.

One or more components of the sample may then be identified from the aligned peaks in signal intensity (Block 214). For example, a reconstructed mass chromatogram containing a synthetic peak in signal intensity versus mass-to-charge, time (e.g., ionization time) for the sample may be generated (Block 216). In some embodiments, the corrected data is used to re-construct a modeled mass chromatogram by using the new peak positions (e.g., bin values) and measured peak intensities for creating synthetic peaks (e.g., by calculating a Gaussian function) around those peak positions and having the measured peak intensities (which may or may not be scaled).

The reconstructed mass chromatogram may then be used in subsequent modeling and analysis (e.g., principle components analysis (PCA), factor analysis (FA), and other methods of deconvoluting spectra). See, e.g., Jolliffe I. T. "Principal Component Analysis" in the *Springer Series in Statistics,* 2nd ed. (Springer, New York (2002)) and A. Gorban, B. Kegl, D. Wunsch, A. Zinovyev (eds.), "Principal Manifolds for Data Visualization and Dimension Reduction", *LNCSE* 58 (Springer, New York (2007)), which are herein incorporated by reference in their entireties. Accordingly, principle components analysis (PCA) or factor analysis (FA) may be performed on the reconstructed mass chromatogram (Block 218). For example, the PCA or FA finds may be used to determine whether the chromatogram indicates that the sample is a one- or multi-component mixture (e.g., a mixture of 2, 3, 4, 5, or more components). Using PCA or factor analysis, the number of latent variables within a given significant region is determined. Using the set of chromatograms from a significant region, signal intensity as a function of bin number is used to determine the principal components and coefficients (e.g., loading vectors and scores) describing the mass chromatogram.

In some embodiments, the data may be used in a subsequent FA. Empirical constraints can be used to facilitate the modeling and analysis. For example, concentrations and intensities are constrained to be non-negative and the concentration profiles are assumed to be Gaussian in shape. In this context, the principle components are related to the modeled concentrations and putative pure component spectra of the putative components of the sample. The putative pure component spectra and the retention times for each component are used to query a database of standard spectra to identify the chemical component or components of the sample. In embodiments, the PCA analysis may further be used to assess the quality of the peak associations assigned from pairs of consecutive scans.

In one or more implementations, the systems, apparatus, and methods described herein may employ databases. In such implementations, the database may comprise libraries of spectroscopic data from known compounds and/or ions. The characteristics of the members of the library may be empirically measured or predicted. Such databases may be accessed to compare data from an experimental sample to data in the library to assist in the identification of an unknown compound or compounds. In implementations, the database may include data for one or more compounds associated with a class of molecules that are expected to be in a tested sample (e.g., volatile organic compounds in an industrial testing use; warfare agents in military use; contaminant analysis in a drug manufacturing use; and so forth). Such data may be used to identify a compound in a sample or to determine that a compound is not one of the library compounds. For example, one or more features (e.g., ions) associated with a compound in the library may be determined not to be present in the experimental sample so that the presence of the library compound can be excluded, even if a definitive identity of the sample compound is not made.

In implementations, a variety of analytical devices can make use of the structures, techniques, approaches, and so on described herein. Thus, although mass spectrometry systems 102 are described herein, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components, and so forth can be constructed in a variety of ways without departing from this disclosure. Rather, the specific features and acts are disclosed as example forms of implementing the claims.

What is claimed is:

1. A method of detecting the presence of a component in a sample of a substance, the method comprising:
    accessing mass spectrometry data stored in a tangible memory, the mass spectrometry data describing signal intensity and ionization time for the sample analyzed by a mass spectrometer, wherein the mass spectrometry data is configured to facilitate the representation of signal intensity versus ionization time for the sample in at least two mass chromatograms;
    processing the mass spectrometry data to identify significant regions for analysis of each of the mass chromatograms;
    identifying peaks in signal intensity within the identified significant regions of the mass chromatograms;
    correcting the peaks in signal intensity with respect to mass-to-charge in the mass chromatograms;
    aligning the at least two mass chromatograms to identify at least one aligned peak in signal intensity; and
    identifying one or more components of the sample from the at least one aligned peak in signal intensity and detecting the presence of the component in the sample based on said identification.

2. The method as recited in claim 1, further comprising processing the mass spectrometry data to adjust a noise baseline of the signal intensity of the mass chromatograms.

3. The method as recited in claim 1, wherein processing of the mass spectrometry data to identify significant regions for analysis of the mass chromatograms comprises applying an exponentially weighted moving average (EWMA) to the mass chromatogram and identifying sample intensities that are at least a predetermined number of standard deviations from a mean sample intensity.

4. The method as recited in claim 1, wherein identifying peaks in signal intensity within the identified significant regions of the mass chromatograms comprises approximating peaks with a Gaussian approximation.

5. The method as recited in claim 1, wherein correcting the peaks in signal intensity with respect to the mass-to-charge in the mass chromatograms comprises applying bin shifting to the peaks in signal intensity.

6. The method as recited in claim 1, wherein identifying one or more components of the sample from the at least one aligned peak in signal intensity comprises generating a reconstructed mass chromatogram containing a synthetic peak in signal intensity versus mass-to-charge for the sample, the synthetic peak derived from the at least one aligned peak in signal intensity.

7. The method as recited in claim 6, wherein identifying one or more components of the sample from the at least one aligned peak in signal intensity comprises performing at least one of principle components analysis (PCA) or factor analysis (FA) to the reconstructed mass chromatogram.

8. A data processing apparatus for detecting the presence of a component in a sample of a substance, the apparatus comprising:
a tangible memory operable to store mass spectrometry data describing signal intensity and ionization time for the sample analyzed by a mass spectrometer, the mass spectrometry data configured to facilitate the representation of signal intensity versus mass-to-charge for the sample in at least two mass chromatograms and a module configured to facilitate analysis of the at least two mass chromatograms; and
a processing system operable to execute the module to:
process the mass spectrometry data to identify significant regions for analysis of the mass chromatograms;
identify peaks in signal intensity within the identified significant regions of the mass chromatograms;
correct the peaks in signal intensity with respect to the mass-to-charge in the mass chromatograms;
align the at least two mass chromatograms to identify at least one aligned peak in signal intensity; and
identify one or more components of the sample from the at least one aligned peak in signal intensity and detect the presence of the component in the sample based on said identification.

9. The data processing apparatus as recited in claim 8, wherein the processing system is further configured to execute the module to process the mass spectrometry data to adjust a noise baseline of the signal intensity of the mass chromatograms.

10. The data processing apparatus as recited in claim 8, wherein the processing system is operable to execute the module to process the mass spectrometry data to identify significant regions for analysis of each of the mass chromatograms by applying an exponentially weighted moving average (EWMA) to the mass chromatogram and identifying sample intensities that are at least a predetermined number of standard deviations from a mean sample intensity.

11. The data processing apparatus as recited in claim 8, wherein the processing system is operable to execute the module to identify peaks in signal intensity within the identified significant regions of each of the mass chromatograms by approximating peaks with a Gaussian approximation.

12. The data processing apparatus as recited in claim 8, wherein the processing system is operable to execute the module to correct the peaks in signal intensity with respect to the mass-to-charge in the mass chromatograms by applying bin shifting to the peaks in signal intensity.

13. The data processing apparatus as recited in claim 8, wherein the processing system is operable to execute the module to identify one or more components of the sample from the at least one aligned peak in signal intensity by generating a reconstructed mass chromatogram containing a synthetic peak in signal intensity versus mass-to-charge for the sample, the synthetic peak derived from the at least one aligned peak in signal intensity.

14. The data processing apparatus as recited in claim 13, wherein the processing system is operable to execute the module to identify one or more components of the sample from the at least one aligned peak in signal intensity by performing at least one of principle components analysis (PCA) or factor analysis (FA) to the reconstructed mass chromatogram.

15. A mass spectrometry system comprising:
a mass spectrometer configured to ionize a sample of a substance to generate charged molecules and to measure the mass-to-charge ratio of the charged molecules and generate mass spectrometry data in response thereto, the mass spectrometry data describing signal intensity and ionization time for the sample; and
a data processing apparatus for detecting the presence of a component in the sample of the substance, said apparatus configured to:
receive the mass spectrometry data from the mass spectrometer, the mass spectrometry data configured to facilitate the representation of signal intensity versus mass-to-charge for the sample in at least two mass chromatograms;
process the mass spectrometry data to identify significant regions for analysis of the mass chromatograms;
identify peaks in signal intensity within the identified significant regions of the mass chromatograms;
correct the peaks in signal intensity with respect to mass-to-charge in the mass chromatograms;
align consecutively one of the at least two mass chromatograms to identify at least one aligned peak in signal intensity; and
identify one or more components of the sample from the at least one aligned peak in signal intensity and detect the presence of the component in the sample based on said identification.

16. The mass spectrometry system as recited in claim 15, wherein the data processing apparatus is further configured to process the mass spectrometry data to adjust a noise baseline of the signal intensity of the mass chromatograms.

17. The mass spectrometry system as recited in claim 15, wherein the data processing apparatus is further configured to process the mass spectrometry data to identify significant regions for analysis of each of the mass chromatograms by applying an exponentially weighted moving average (EWMA) to the mass chromatogram and identifying sample intensities that are at least a predetermined number of standard deviations from a mean sample intensity.

18. The mass spectrometry system as recited in claim 15, wherein the data processing apparatus is further configured to identify peaks in signal intensity within the identified significant regions of each of the mass chromatograms by approximating peaks with a Gaussian approximation.

19. The mass spectrometry system as recited in claim 15, wherein the data processing apparatus is further configured to correct the peaks in signal intensity with respect to the mass-to-charge in the mass chromatograms by applying bin shifting to the peaks in signal intensity.

20. The mass spectrometry system as recited in claim 15, wherein the data processing apparatus is further configured to identify one or more components of the sample from the at least one aligned peak in signal intensity by generating a reconstructed mass chromatogram containing a synthetic peak in signal intensity versus mass-to-charge for the sample, the synthetic peak derived from the at least one aligned peak in signal intensity.

\* \* \* \* \*